United States Patent
Amasino et al.

(10) Patent No.: US 7,199,282 B2
(45) Date of Patent: Apr. 3, 2007

(54) FLORAL INDUCTION GENE

(75) Inventors: Richard M. Amasino, Madison, WI (US); Fritz M. Schomburg, Madison, WI (US); Scott D. Michaels, Madison, WI (US); David Patton, Basel (CH)

(73) Assignee: Wisconsin Alumni Research Foundation, Madison, WI (US)

( * ) Notice: Subject to any disclaimer, the term of this patent is extended or adjusted under 35 U.S.C. 154(b) by 425 days.

(21) Appl. No.: 09/920,705

(22) Filed: Aug. 2, 2001

(65) Prior Publication Data

US 2003/0079252 A1  Apr. 24, 2003

Related U.S. Application Data

(60) Provisional application No. 60/222,550, filed on Aug. 3, 2000.

(51) Int. Cl.
*C12N 15/29* (2006.01)
*C12N 15/82* (2006.01)
*A01H 5/00* (2006.01)
*A01H 5/10* (2006.01)

(52) U.S. Cl. .................... 800/278; 800/298; 800/290; 800/287; 536/23.6

(58) Field of Classification Search ............... 800/298, 800/290, 287, 278; 435/468
See application file for complete search history.

(56) References Cited

U.S. PATENT DOCUMENTS 6,096,946 A * 8/2000 Roberts et al. ............. 800/290

FOREIGN PATENT DOCUMENTS

WO   WO 96/38560      12/1996
WO   WO 00/32780   *  6/2000

OTHER PUBLICATIONS

Kano-Murakami et al (1993, FEBS 334:365-368).*
Fire, A., "RNA-triggered gene silencing," TIG 15(a): 358-363 (Sep. 1999).
"AA06B09 AA *Arabidopsis thaliana* cDNA5', mRNA sequence." *Database EMBL 'Online*, (Jun. 14, 2000), Database accession No. BE037904 XP002213594.
"*Arabidopsis thaliana* CDNA clone:RZL51g08F, 3' end." *Database EMBL 'Online*, (Jun. 16, 2000), Database accession No. AV548323 XP002213595.

"*Arabidopsis thaliana* chromosome 2 clone T1O24 map CIC10F102, complete sequence." *Databse EMBL 'Online*, (Jul. 24, 1997), Database accession No. AC002335 XP002213591.
"*Arabidopsis thaliana* chromosome 4, BAC clone T1P17 (ESSA Project)." *Database EMBL 'Online*, (Apr. 29, 1999), Database accession No. AL049730 XP002213608.
"At2g43410 protein." *Database SWISSPROT Online*, (Jan. 1, 1998), Database accession No. 022855, XP002213592.
"Hypothetical 78.3 kDa protein." *Database SWISSPROT Online*, (May 1, 2000), Database accession No. Q9SU22, XP002213609.
RNA-binding region RNP-1 "RNA recognition motif." *Database SWISSPROT Online*, (Jan. 1, 1998), Database accession No. IPR000504, XP002213593.
Koornneef M, Alonso-Blanco C, Blankestijn-de Vries H, Hanhart CJ, Peeters AJ. "Genetic interactions among late-flowering mutants of *Arabidopsis*." *Genetics*, (Feb. 1998) 148(2):885-92.
Levy YY, Dean C. "The transition to flowering." *Plant Cell*, (Dec. 1998) 10(12):1973-90.
Macknight R, Bancroft I, Page T, Lister C, Schmidt R, Love K, Westphal L, Murphy G, Sherson S, Cobbett C, Dean C. "FCA, a gene controlling flowering time in *Arabidopsis*, encodes a protein containing RNA-binding domains." *Cell*, (May 30, 1997) 89(5):737-45.
Michaels SD, Amasino RM. "*Flowering Locus* C encodes a novel MADS domain protein that acts as a repressor of flowering." *Plant Cell*. (May 1999) 11(5):949-56.
Ruiz-Garcia L, Madueno F, Wilkinson M, Haughn G, Salinas J, Martinez-Zapater JM. "Different roles of flowering-time genes in the activation of floral initiation genes in *Arabidopsis*." *Plant Cell*, (Nov. 1997) 9(11):1921-34.
Sanda SL, Amasino RM. "Interaction of FLC and late-flowering mutations in *Arabidopsis thaliana*." *Mol Gen Genet.*, (Apr. 24, 1996) 251:69-74.
Hecht V, et al., "Conservation of *Arabidopsis* flowering genes in model legumes," Plant Physiol. 137:1420-1434 (2005).
Brunner A & Nilsson O, "Revisiting tree maturation and floral initiation in the poplar functional genomics era," New Physiologist 164:43-51 (2004).

* cited by examiner

*Primary Examiner*—Stuart F. Baum
(74) *Attorney, Agent, or Firm*—Quarles & Brady LLP

(57) ABSTRACT

The present invention provides an FPA polynucleotide sequence which is involved in controlling the flowering time of plants. The present invention also provides a vector incorporating the protein coding sequence, or a portion or homolog thereof, as well as a genetically modified plant. Also disclosed are methods of producing a genetically modified plant in which the flowering time of the plant has been selectively altered, and methods for reducing the activity of FLC mRNA in plants containing the FLC gene.

17 Claims, No Drawings

FLORAL INDUCTION GENE

CROSS-REFERENCE TO RELATED APPLICATIONS

This application claims the benefit under 35 U.S.C. §119(e) of U.S. Provisional Application No. 60/222,550 filed Aug. 3, 2000.

STATEMENT REGARDING FEDERALLY SPONSORED RESEARCH OR DEVELOPMENT

This invention was made with United States government support awarded by NSF Grant No. 9318481. The United States has certain rights in this invention.

BACKGROUND OF THE INVENTION

The present invention relates to the control of flowering time in plants using genetic engineering. Specifically, this invention relates to the control of flowering time in plants by manipulation of the activity of the FPA gene.

In growing plantlets, the transition from vegetative growth to flowering is the major developmental switch in the plant life cycle. The timing of this transition to a flowering state is critical for the plant's reproductive success. Accordingly, most plant species have evolved systems to precisely regulate flowering time. These systems monitor both environmental cues and the developmental state of the plant.

Photoperiod and temperature are two environmental cues commonly monitored by plants. In plants responsive to photoperiod cues so examined, flowering is promoted by flowering signals which are translocated from leaves to meristems as leaves detect day length changes (Zeevaart, *Light and the Flowering Process*, 137–142 (Eds., D. Vince-Prue, B. Thomas and K. E. Cockshull, Academic Press, Orlando, 1984)). In temperature-responsive plants, exposure to cold temperatures promotes flowering by a process known as vernalization. Vernalization affects meristems directly, perhaps by causing them to become competent to perceive flowering signals (Lang, *Encyclopedia of Plant Physiology*, 15(Part 1):1371–1536, (ed., W. Ruhland, Springer-Verlag, Berlin, 1965)). Other environmental cues that can affect flowering include light quality and nutritional status.

The developmental state of the plant can also influence flowering time. Most species go through a juvenile phase during which flowering is suppressed and then undergo a transition to an adult phase in which the plant becomes competent to flower (Poethig, *Science*, 250:923–930 (1990)). This "phase change" permits the plant to reach a proper size for productive flowering.

The influence of the development state of a plant on flowering timing is controlled along developmental flowering pathways. In the flowering literature, the developmental flowering pathways are often referred to as autonomous to indicate that they do not involve the sensing of environmental variables. However, it is unlikely that the autonomous and environmental pathways are entirely distinct. For example, day-neutral species of tobacco typically flower after producing a specific number of nodes and, thus, could be considered as flowering entirely through an autonomous pathway. However, grafting studies have indicated that both day-neutral and photoperiod-responsive tobacco species respond to similar translocatable flowering signals (Lang et al., *Proc. Natl. Acad. Sci., USA*, 74:2412–2416 (1977); McDaniel et al., *Plant J.*, 9:55–61 (1996)). Accordingly, aspects of the underlying biochemistry of these pathways appear to be conserved.

Genetic analyses of several species has identified genes that affect the time in which a plant begins to flower. The most extensive genetic analysis of these genes has been performed in the plant species, *Arabidopsis thaliana*.

In *Arabidopsis*, genes which control flowering timing have been identified by two approaches. One approach has been to induce mutations in early-flowering varieties so as to elicit either late-flowering or early-flowering. Late-flowering mutations identify genes whose wild-type role is to promote flowering, while early-flowering mutations identify genes that inhibit flowering. Studies in *Arabidopsis* have identified over 20 loci whose mutations specifically affect flowering time, and several other loci that affect flowering time as well as other aspects of development (e.g., det2, cop1, gal and phyB) (Koornneef et al., *Ann. Rev. Plant Physiol., Plant Mol. Biol.*, 49:345–370 (1998); Weigel, *Ann. Rev. Genetics*, 29:19–39 (1995)).

A second approach to identifying flowering timing genes is to determine the genetic basis for the naturally occurring variations in flowering time. Although early-flowering *Arabidopsis* varieties are the most commonly used varieties in the lab, most *Arabidopsis* varieties are actually late-flowering. Late-flowering varieties differ from early-flowering varieties in that the late-flowering varieties contain dominant alelles at two loci, FRIGIDA (FRI) and FLOWERING LOCUS C (FLC), which suppress flowering (Sanda et al., *Plant Physiol.*, 111:641–645 (1996); Lee et al., *Plant Journal*, 6:903–909 (1994); Clarke et al., *Mol. Gen. Genet.*, 242:81–89 (1994); Koornneef et al., *Plant Journal*, 6:911–919 (1994)).

Physiological analyses of the flowering timing mutants and the naturally occurring flowering timing variations indicate that flowering is controlled in *Arabidopsis* by multiple pathways (Koornneef et al., *Ann. Rev. Plant Physiol., Plant Mol. Biol.*, 49:345–370 (1998)). For example, plants containing one group of late-flowering mutants (fca, fpa, fve, fy, ld) and plants containing the late-flowering FLC and FRI alleles are delayed in flowering during inductive (long-day) conditions and more severely delayed during short-day conditions. Studies have shown that vernalization of these late-flowering lines can suppress the late-flowering phenotype. Another group of late-flowering mutants (co, fd, fe, fha, ft, fwa, gi) exhibit minimal or no difference in flowering time when grown in short days compared to long days. This group also shows little or no response to vernalization. Moreover, double mutants within a group do not flower later than either single-mutant parent, whereas double mutants containing a mutation in each group flower later than the single-mutant parents (Koornneef et al., *Genetics*, 148:885–92 (1998)). A separate autonomous pathway appears to control the age or, more specifically, the developmental stage at which plants are competent to flower. This pathway is referred to as autonomous because mutations in this pathway do not affect the plant's photoperiod response. Recent studies of these mutations have shown changes in these mutants, such as alterations of trichome patterns, which indicate that such mutant plants are delayed in transitioning from the juvenile to adult states (Telfer et al., *Development*, 124:645–654 (1997)). Accordingly, there appears to exist parallel flowering pathways which mediate flowering time in response to environmental and developmental cues.

The time in which plants flower is of great importance in both agricultural and horticultural crops. In horticultural crops, the product is often the flower, while in food, feed or fiber crops, the product is often the flower and/or the products of flowering (i.e., fruits, seeds, or seedpods). Understanding the molecular aspects of flowering timing control in these crops will lead to strategies for optimizing flower, fruit, and seed production. For example, accelerating the onset of flowering in certain crops may permit those crops to be grown in regions where the growing season is otherwise too short, or permit multiple crops to be grown in regions where only one crop is currently possible. In addition, preventing or substantially delaying flowering will increase the yield of the useful parts of certain crops. For example, delaying or preventing flowering in forage crops (e.g., alfalfa and clover) and vegetables crops (e.g., cabbage and related Brassicas, spinach, and lettuce) should increase crop yields. Likewise, the yields of crops in which underground parts are used (e.g., sugar beets or potatoes), may also be increased by delaying or preventing flowering. In sugar beets, the prevention of flowering will also permit more energy to be devoted to sugar production. Likewise the yield of wood and biomass crops may also be increased by delaying flowering.

SUMMARY OF THE INVENTION

The present invention is summarized in that a novel FPA protein coding sequence has been isolated and used to affect the flowering time of plants by altering the level of FPA protein activity in the cells of the plant.

The present invention includes a plant comprising in its genome a transgene encoding an FPA polynucleotide sequence, wherein the transgene alters the timing of the plants flowering as compared to non-transgenic plants of the same species. The plant may be genetically modified by the introduction of the FPA polynucleotide sequence in either the sense or antisense orientation.

The present invention also includes a genetic construct comprising an FPA polynucleotide sequence and a promoter that promotes expression of the sequence in plants. The present invention is also directed towards polynucleotide sequences representing genes that function in regulating FPA protein activity, and which, when expressed, alter the flowering time of the plant in which it is introduced.

The present invention also includes a method for altering the flowering time of a plant using the FPA polynucleotide sequence described above, and a method for down-regulating FLC mRNA activity using the FPA polynucleotide sequence described above.

The present invention is also a seed, comprising in its genome a genetic construct comprising an FPA polynucleotide sequence and a promoter that promotes gene expression in plants.

The present invention is also a plant cell comprising in its genome a genetic construct comprising an FPA polynucleotide sequence and a promoter capable of promoting gene expression in plants.

It is an object of the present invention to provide a method and a tool for altering the flowering timing in plant species. The flowering timing can be made earlier or later by affecting the level of the FPA protein in such plants.

Other objects advantages and features of the present invention will become apparent from the following specification.

BRIEF DESCRIPTION OF THE DRAWINGS

None.

DETAILED DESCRIPTION

The present invention is directed at the nucleotide and protein sequences for the FPA gene in plants. The FPA gene has been discovered to be a gene which acts to promote floral induction in plants during both long and short day photoperiods. It is disclosed here that the absence or suppression of FPA activity in plants results in a delay of floral induction in both long and short day photoperiods, while the added expression of FPA in plants causes an earlier flowering timing relative to non-transgenic plants of the same species.

The lifetime of a plant can be divided into at least two phases referred to as the vegetative phase and the reproductive phase. During the vegetative phase, most commercially important crop plants grow continuously, increasing in both size and leaf number, until the reproductive phase is reached. The reproductive phase begins with flowering initiation. At that point much of the plant's further growth is directed towards the growth (or development) of flowers, fruits, and seeds utilized in reproduction.

We have discovered that the *Arabidopsis* FPA gene is capable of altering floral induction in a wide range of genetic and physiologic conditions such that it is anticipated that the FPA gene may be a useful tool for regulating the flowering time in many plant species. For example, the FPA gene can accelerate flowering in several late-flowering mutant backgrounds (e.g., fve-2 and fca-1), and can fully compensate for the addition of two naturally occurring genes, FRI and FLC, which confer late-flowering phenotypes. Because FRI and FLC may be responsible for regulating the flowering time in plant species other than *Arabidopsis,* it is anticipated that the FPA gene may also be capable of altering the flowering time of such species as well. Our studies have also shown that the overexpression of FPA can compensate for the delaying effect caused by short days on floral induction. Accordingly, the added expression of FPA may be used to alter the flowering time in species having a photoperiod requirement for flower initiation. In addition, our studies have shown that the overexpression of FPA has the additional effect of decreasing FLC mRNA in plants containing the FLC gene, suggesting that FPA may be a useful tool for down-regulating FLC activity.

The present invention provides a method for altering the time of flower initiation in a plant by introducing into the genome of the plant an FPA polynucleotide sequence capable of up-regulating or down-regulating FPA activity in the cells of the plant. Upon introduction into the genome of a plant, the FPA polynucleotide sequence can act to augment the activity of an endogenous gene regulating the time in which the plant would typically initiate flowering. For instance, a second copy of the FPA gene can be introduced into a plant to increase the amount of FPA activity present in the plant and cause early-flowering. Expression of a portion of a polypeptide encoded by the FPA gene can also lead to a delay of flowering in a plant. This polypeptide portion which leads to the delay of flowering in a plant can be referred to as a dominant negative mutant. Fragments of the FPA gene can also act to decrease activity of an endogenous FPA gene by modifying the expression of the endogenous FPA gene. For instance, expression of the complement of the FPA gene can result in an antisense RNA fragment which will suppress FPA activity and lead to delay the activation of the flowering time in the plant. In addition, the expression of an FPA polynucleotide sequence of the present invention may also result in a delay of flowering by cosuppression. Another method to alter the activity of the FPA gene is to introduce into a plant's genome a fragment that encodes an antibody or other polypeptide that would bind to the FPA gene, or its RNA, or a protein encoded by the FPA gene and render it inactive or less active.

The present invention also provides a method for altering FLC mRNA activity in plants containing the FLC gene by introducing into the genome of the plant an FPA polynucleotide sequence capable of suppressing FLC MRNA activity. Upon introduction into the genome of a plant, the FPA polynucleotide sequence may either increase the amount of FPA activity present in the plant to cause a decrease in FLC mRNA activity, or cause the expression of a portion of a polypeptide or nucleotide sequence which leads to a decrease in FLC mRNA activity. In general, FLC MRNA is upregulated by the presence of the FRIGIDA (FRI) gene. In the genetic background in plants containing both FRI and FLC, FLC represses flowering based on the quantity of the FLC message. Accordingly, overexpression of FPA in a FRI/FLC containing plant results in the removal of FLC message and concurrent early flowering.

The identification and characterization of the FPA gene from *Arabidopsis thaliana* is described in the examples below. While this gene has existed previously in its native, or altered, state in plants, this disclosure is believed to be the first disclosure of the FPA gene in its isolated form. By isolated form, it is meant that the genes have been isolated from their host plants. The sequence for the entire FPA gene is set forth in SEQ ID NO:1. The cDNA protein coding sequence for the FPA gene is set forth in SEQ ID NO:2, and its deduced amino acid sequence is set forth in SEQ ID NO:3. An analysis of this data indicates that the FPA gene shares some sequence homology with other known RNA binding proteins. Because of the high degree of sequence homology across plant species, it is anticipated that the present invention is capable of use in a large number of plants. In addition, it is anticipated that the FPA polynucleotide sequence of the present invention may also be used to isolate other FPA genes in other plant species in order to obtain other FPA polynucleotide sequences having similar effects.

As used herein, "FPA" refers to the *Arabidopsis* FPA gene (SEQ ID NO:1), as well as the FPA cDNA (SEQ ID NO:2) and the analogous gene sequences from other plants, and the variations and mutants thereof which retain flowering functionality. It is expected that most flowering plants contain FPA genes homologous to the *Arabidopsis* FPA gene. Given the high degree of sequence homology across plant species, it is reasonable to expect that FPA genes from any plant, of which the *Arabidopsis* FPA gene is but one example, could be used in the practice of the present invention. For example, FPA genes from plants that are raised for their agricultural or horticultural value may be used in the practice of the present invention.

It is specifically contemplated that any FPA polynucleotide sequence could be used in the practice of the present invention. "FPA polynucleotide sequence" is defined to include any plant DNA sequence which expresses an FPA gene, or which is capable of overexpressing or reducing the expression of the FPA gene native to the plant in which the FPA polynucleotide sequence is introduced. An FPA polynucleotide sequence may be an unmodified sequence (such as SEQ ID NO:1) isolated from any plant, a cDNA sequence (such as SEQ ID NO:2) derived from any plant, a genomic or cDNA sequence that is modified to contain minor nucleotide additions, deletions, or substitution, or a synthetic DNA sequence. The term is also intended to apply to analogous sequences from other plants as well as allelic variations and mutations which are still capable of controlling FPA activity.

Analogous sequences (homologs) include genes from *Arabidopsis* and other plant species having a certain percentage of identity with SEQ ID NO:2. Identity is a relatedness that can be determined by, but not limited to, nucleic acid hybridization techniques, computer searches of databases, computer or manual comparisons of amino acid and nucleotide sequences, and protein detection with the use of FPA-specific antibodies. Two analogous nucleotide sequences are "similar" if they can be aligned so that a percentage of corresponding residues are identical. For example, two nucleotide sequences are analogous if the have greater than about 31%, more preferably at least about 50%, even more preferably at least about 70%, and most preferably at least about 80% identity to each other.

Homologs also include polypeptides from *Arabidopsis* and other species having a certain level of identity with the polypeptide encoded by SEQ ID NO:1 or SEQ ID NO:2. Homologs also include coding regions and polypeptides that function comparable to an FPA coding region on an FPA polypeptide. For example, a polypeptide homolog includes, without limitation, a polypeptide having greater than about 31%, more preferably at least about 50%, even more preferably at least about 70%, and most preferably at least about 80% identity to the RNA binding region of the FPA protein. Whether a coding region or a polypeptide is an homolog can be determined by expressing the coding region and/or the polypeptide in *Arabidopsis* and evaluating the effect on flower initiation. Described in the examples below are tests to determine whether a particular FPA gene does, in fact, act to delay or promote flowering. By testing these genes, using *Arabidopsis* as a model, the activity of a particular FPA gene can be confirmed.

FPA polynucleotide sequence is also intended to include fragments of an FPA gene which are capable of altering the time of flower initiation in a plant. Such fragments include polymeric forms of nucleotides of any length, either ribonucleotides or deoxynucleotides, and includes both double- and single-stranded DNA (both genomic and cDNA) and both double- and single-stranded RNA. A fragment may also include both coding and non-coding regions that can be obtained directly from a natural source (e.g., a plant), or can be prepared with the aid of recombinant or synthetic techniques. Fragments also include polynucleotide sequences, wherein the complement of the polynucleotide sequence hybridizes to SEQ ID NO:1 or SEQ ID NO:2 under standard hybridization conditions. During hybridization the entire nucleotide sequence of the complement can hybridize with SEQ ID NO:1 or SEQ ID NO:2, or a portion thereof. Preferably, at least about 20 nucleotides of the complement hybridize with SEQ ID NO:1 or SEQ ID NO:2, more preferably at least about 50 nucleotides, and most preferably at least about 100 nucleotides. In the preferred embodiment, such fragments include those encoding a polypeptide which is involved in altering the timing of flower initiation in a plant. Portions of such a polypeptide and homologs of such a polypeptide are also included in the present invention, provided they have the ability to alter the time of flower initiation.

By "transgene" it is meant to describe an artificial genetic construction carried in the genome of a plant and inserted in the plant or its ancestor by gene transfer. Such transgenes are transmissible by normal Mendelian inheritance once inserted. By "transgenic plant" it is meant any plant modified by the introduction of a transgene into the genome of one or more plant cells, which can generate whole, sexually competent, viable plants.

As used herein, the term "isolated" means that a polypeptide or polynucleotide fragment is either removed from its natural environment or synthetically derived. Preferably, the polypeptide or polynucleotide is purified, i.e., essentially free from any other polypeptides or polynucleotides, respectively, and associated cellular products or other impurities.

"Polypeptide" as used herein refers to a polymer of amino acids and does not refer to a specific length of a polymer of amino acids. Thus, for example, the terms peptide, oligopeptide, protein, and enzyme are included within the definition of polypeptide. This term also includes post-expression modifications of the polypeptide, for example, glycosylations, acetylations, phosphorylations, and the like. "Percentage amino acid identity" refers to a comparison of the amino acids of two polypeptides as described herein.

"Flower initiation" refers to the transition of a shoot meristem to the formation of flower primordia. Flower initiation can be determined by microscopic analysis to determine the formation of flower primordia, or by the naked eye. The "leaves" of a plant present at flower initiation include all the leaves present on a plant.

A "coding region" is a linear form of nucleotides that encodes a polypeptide, usually via mRNA, when placed under the control of appropriate regulatory sequences. The complement of the coding region can encode an antisense RNA polynucleotide fragment when placed under the control of appropriate regulatory sequences. The boundaries of a coding region are generally determined by a translation start codon at its 5' end and a translation stop codon at its 3' end. "Expression" of a coding region refers to those processes that are required to result in a polypeptide, including, for instance, transcription of the coding region and translation of the mRNA encoded by the coding region.

The present invention provides for a transgenic plant having in its genome a transgene containing a sense or antisense FPA polynucleotide sequence which causes the plant to have an altered flowering time as compared to non-transgenic plants of the same species. The FPA polynucleotide sequence may include, without limitation, sequences which encode polypeptides involved in the promotion of flowering, or produce antisense RNA, or are part of a construct involved in cosuppression, or encode an antibody or other binding polypeptides that inactivate or reduce FPA activity. Also provided are plant cells and plant tissues derived from the transgenic plant of the present invention, and seeds which can germinate into a transgenic plant described herein.

Plants included in the invention are any flowering plants amenable to transformation techniques, including both monocotyledonous and dicotyledonous plants. Examples of monocotyledonous plants include, but are not limited to, vegetables such as asparagus, onions and garlic; cereals such as maize, barley, wheat, rice, sorghum, pearl millet, rye and oats; and grasses such as forage grasses and turfgrasses. Examples of dicotyledonous plants include, but are not limited to, vegetables, feed, and oil crops such as tomato, beans, soybeans, peppers, lettuce, peas, alfalfa, clover, Brassica species (e.g., cabbage, broccoli, cauliflower, brussel sprouts, rapeseed, and radish), carrot, beets, eggplant, spinach, cucumber, squash, melons, cantaloupe, sunflowers; fiber crops such as cotton; and various ornamentals such as flowers and shrubs.

It is specifically envisioned that transgenic plants according to the present invention can be made with a transgene for an FPA polynucleotide sequence which selectively down-regulates or up-regulates FPA activity. Several techniques are known in the art for either down-regulating or up-regulating the activity of such endogenous plant genes. For example, extra copies of the FPA gene (SEQ ID NO:1) or its cDNA (SEQ ID NO:2) can be introduced into a plant to up-regulate FPA activity. On the other hand, a polynucleotide fragment encoding an FPA antisense RNA (i.e., SEQ ID NO:4) or cosuppression construct can be used to down-regulate FPA activity. A construct producing an antisense RNA would generally include a promoter driving the production of an antisense RNA polynucleotide molecule complementary to an mRNA produced by the FPA gene. The antisense RNA polynucleotide can be a portion of the corresponding FPA mRNA, as it has been demonstrated that such portions can function effectively to suppress gene expression (Bariola et al., *Plant Physiol.*, 119, 331–342 (1999); Kang et al., *Plant Mol. Biol.*, 38, 1021–1029, 1998).

Another down-regulating method is to use cosuppression. Cosuppression is a poorly understood phenomenon by which insertion of an artificial gene construct into a plant occasionally causes suppression of both the inserted gene and any other gene homologous to it. In general, a cosuppression construct will raise the level of FPA mRNA, or a fragment of the mRNA, to a level that the cell will decrease expression of both the endogenous FPA gene and transgene (Kasschau et al., *Cell*, 95, 461–470, 1998). Cosuppression can occur by introducing an FPA polynucleotide fragment that includes an FPA coding region (i.e., SEQ ID NO:6), or portion thereof (i.e., SEQ ID NO:5), which is identical to the endogenous FPA coding region.

Another method to modify FPA activity is to introduce into a plant's genome a polynucleotide fragment that encodes an antibody or other polypeptide that would bind to the FPA polypeptide and render it inactive or less active.

Another method to modify FPA activity is to introduce into a plant's genome polynucleotide fragments encoding dominant-negative versions of a flower time regulation polypeptide. Dominant-negative mutants are proteins that actively interfere with the function of normal, endogenous proteins. Thus, the action of a gene can be blocked without inactivating the structural gene itself or its RNA.

Transgenic plants of the invention are produced by contacting a plant cell with a genetic construction, for example, that includes a FPA polynucleotide sequence as described above. To be effective once introduced into plant cells, the FPA polynucleotide sequence is typically operably associated with a promoter capable of causing transcription and expression of a the polypeptide or mRNA encoded by the FPA polynucleotide sequence. A polyadenylation sequence or transcription control sequence, also recognized in plant cells, may also be employed. It is preferred that the genetic construction harboring the FPA polynucleotide sequence also contain one or more selectable marker genes so that the transformed cells can be selected from nontransformed cells in culture.

The transformation of plants in accordance with the invention may be carried out in essentially any of the various ways known to those skilled in the art of plant molecular biology. As used herein, the term "transformation" means alteration of the genotype of a host plant by the introduction of an FPA polynucleotide fragment of the present invention.

For example, an FPA polynucleotide fragment can be introduced into a plant cell utilizing i Agrobacterium tumefaciens mediated transformation. This method of transformation requires that the FPA polynucleotide sequence be incorporated into the transferred DNA region (T-DNA) of a plasmid that can replicate in Agrobacterium. Methods involving the use of Agrobacterium include, but are not limited to: 1) co-cultivation of Agrobacterium with cultured protoplasts; 2) transformation of plant cells or tissues with Agrobacterium; or 3) transformation of seeds or shoots by infiltration of a suspension of Agrobacterium cells as described by (Bechtold et al., *C. R. Acad. Sci. Paris*, 316, 1194, 1993) and exemplified in the Examples herein.

Alternatively, a FPA polynucleotide sequence can be introduced into a plant cell by contacting the plant cell using mechanical, electrical, or chemical means. For example, the sequence can be mechanically transferred by microinjection directly into plant cells by use of micropipettes. Alternatively, the sequence may be transferred into the plant cell by using polyethylene glycol which forms a precipitation complex with genetic material that is taken up by the cell. The FPA polynucleotide sequence can also be introduced into plant cells by electroporation (Fromm et al., *Proc. Natl. Acad Sci., U.S.A.*, 82, 5824, 1985). In this technique, plant protoplasts are electroporated in the presence of vectors or nucleic acids containing the relevant polynucleotide fragments. Electrical impulses of high field strength reversibly permeabilize membranes allowing the introduction of nucleic acid molecules. Electroporated plant protoplasts reform the cell wall, divide and form a plant callus. Selection of the transformed plant cells with the transformed FPA polynucleotide sequences can be accomplished using phenotypic markers as are well known in the art.

Another method for introducing the FPA polynucleotide sequences of the present invention into a plant cell is by high velocity ballistic penetration using small particles with the sequences to be introduced contained either within the matrix of small beads or particles, or on the surface thereof (Klein et al., *Nature*, 327, 70, 1987).

Viruses such as the Cauliflower mosaic virus (CaMV) may also be used as a vector for introducing the FPA polynucleotide sequences into plant cells (U.S. Pat. No. 4,407,956). The CaMV viral DNA genome is inserted into a parent bacterial plasmid creating a recombinant DNA molecule which can be propagated in bacteria. After cloning, the recombinant plasmid again may be cloned and further modified by introduction of the desired polynucleotide sequence. The modified viral portion of the recombinant plasmid is then excised from the parent bacterial plasmid, and used to inoculate the plant cells or plants.

The experience to date in the technology of plant genetic engineering is that the method of gene introduction is not of particular importance in the phenotype achieved in the transgenic plant. Once the plant has been genetically engineered, and a transgenic plant has been created, the method of transformation of the original plant becomes irrelevant. A transgene inserted into the genome of one plant is then fully inheritable by progeny plants of the original genetically engineered plant by normal rules of classical plant breeding.

To make a transgenic plant, as is known to those of skill in the art, one needs to make a genetic construction capable of expressing the inserted protein coding sequence, whether foreign or endogenous, in the plant to which it has been introduced. The tools and techniques for making genetic constructions that will express proteins in plants are widely known in the art of plant genetics. In general, such genetic constructions include a polynucleotide sequence (e.g., the coding region, or a portion thereof, of the FPA gene) operably associated with a promoter capable of promoting expression of the polynucleotide sequence in the plant.

The promoter used in the genetic construction of the present invention can be either a constitutive promoter or an inducible promoter. Examples of constitutive promoters useful in plant genetic constructions include, without limitation, the 35S RNA and 19S RNA promoters of the cauliflower mosaic virus (Brisson et al., *Nature*, 310, 511, 1984); the opine synthase promoters carried on the tumor-inducing plasmids of Agrobacterium tumefaciens such as the nopaline synthase promoter (Ebert et al., *PNAS*, 84, 5745, 1987) and the mannopine synthase promoter (Velten et al., *EMBO J.* 3, 2723 1984). Tissue-specific promoters may also be used in the present invention. An example of a tissue-specific promoter is the H4A748 promoter expressed in shoot meristems (Atanassova et al., *Plant J.*, 2, 291, 1992).

An inducible promoter suitable for use in the present invention should: 1) provide undetectable or minimal expression in the absence of an inducer; 2) provide sufficiently high expression in the presence of an inducer to produce the desired modification of flowering time; and 3) induce expression of the desired polypeptide or MRNA without substantially altering the physiology of the plant material (other than the effects of the polypeptide itself). Examples of inducible promoters suitable for use in the present invention include, but are not limited to, heat shock promoters such as soybean hsp17.5E or hsp17.3 (Gurley et al., *Mol. Cell Biol.* 6, 559, 1986), light-regulated promoters such as the promoter for the small subunit or ribulose bisphosphate carboxylase (ssRUBISCO) (Coruzzi et al., *EMBO J.* 3, 1671, 1984; Broglie et al., *Science* 224, 838, 1984), chemical-regulated promoters such as Maize ln2-1 and 2-2 which are regulated by benzenesulfonarnides e.g., herbicide safeners (Hershey et al., *Plant Mol. Biol.*, 17, 679, 1991) and alcA and alcR promoter/transcription factor system that is induced by the application of ethanol (Caddick et al., *Nat. Biotech.*, 16, 177, 1998). Other promoters of gene expression will be known to those skilled in the art.

The promoter utilized should be capable of producing sufficient expression of the FPA protein or a portion thereof, or RNA (including part of the RNA sequence or the RNA sequence in entirety to cause cosuppression or an antisense RNA expression) to modify the flowering time of the plant. The promoters used in the constructs of the present invention may be altered, if desired, to modify their expression characteristics.

Optionally, a selectable marker may be associated with the FPA polynucleotide sequence. As used herein, the term "marker" refers to a gene encoding a trait or a phenotype which permits the selection of, or the screening for, a plant or plant cell containing the marker. Preferably, the marker gene is an antibiotic resistance gene whereby the appropriate antibiotic can be used to select for transformed cells from among cells that are not transformed. Examples of suitable selectable markers include adenosine deaminase, dihydrofolate reductase, hygromycin-B-phosphotransferase, thymidine kinase, xanthine-guanine phospho-ribosyltransferase and amino-glycoside 3'-O-phosphotransferase II (which confers kanamycin, neomycin and G418 resistance). Other suitable markers will be known to those of skill in the art.

Transgenic plants according to the present invention may exhibit early or late flowering initiation dependent upon the transgene introduced into the plant. For example, flowering initiation (on average) in a transgenic plant having a transgene that down-regulates FPA activity may occur at least about 3 days, or at least about 7 days, or at least about 12 days, or at least 30 days, or at least about 60 days after initiation of flowering in the same plant without the transgene. Alternatively, flowering initiation (on average) in a transgenic plant having a transgene that up-regulates FPA activity may occur at least about 3 days, or at least about 7 days, or at least about 12 days, or at least about 30 days, or at least about 60 days before initiation of flowering in the same plant without the transgene.

The difference in the length of time to the onset of the flowering stage of a transgenic plant relative to a non-transgenic plant can also be measured by determining the difference in the number of leaves at the time of flower initiation on the transgenic plant as compared to a non-transgenic plant of the same species. Preferably, the transgenic plant having a transgene which down-regulates FPA activity exhibits at least about 50% more, preferably at least about 100% more, more preferably at least about 400% more, and most preferably at least about 800% more leaves at flower initiation than the non-transgenic plant. Alternatively, the transgenic plant having a transgene which up-regulates FPA activity exhibits at least about 10% fewer, preferably at least about 50% fewer, and most preferably at least about 80% fewer leaves at flower initiation than the same non-transgenic plant.

Isolated FPA polynucleotide sequences of the invention can be obtained by several methods. For example, they can be isolated using procedures which are well known in the art. These include, but are not limited to: 1) hybridization of detectably labeled probes representing all or part of the *Arabidopsis* FPA gene to genomic or cDNA libraries to detect similar nucleic acid sequences; 2) antibody screening of expression libraries to detect similar structural features; 3) synthesis by the polymerase chain reaction (PCR); and 4) chemical synthesis of a nucleic acid molecule. Sequences for specific coding regions of genes can also be found in GenBank, the National Institutes of Health computer database. The coding region can then be isolated and ligated into a vector as is well known in the art. Probes useful in the invention include those made using the entire FPA coding region or portions thereof.

FPA belongs to a class of genes known as RNA-binding proteins. These genes and the polypeptides they encode typically have several conserved domains. The RNP2/RNP1 RNA binding regions contain similarity to other members of the family of RNA-binding proteins. Therefore, probes that contain these regions may be useful in the isolation of FPA-homologous sequences. Additionally, RNA-binding proteins also contain other domains useful for identification of homologues (such as an acidic C-terminus). Probes to these less conserved regions may also be used to isolate FPA homologues.

In a preferred embodiment, the invention includes a method of producing a genetically modified plant characterized as having modified timing of flowering, said method comprising constructing a genetic construct as described above; introducing the construct into a plant cell; growing a plant from said transformed plant cell and selecting a plant that has received the genetic construct; and growing the plant under conditions that allow expression of the FPA polynucleotide sequence to alter the flowering time of the plant. As used herein, the term "introducing" refers to any means of introducing the transgene into the plant cell, including chemical and physical means as described above.

Normally, a transformed plant cell is regenerated to obtain a whole plant from the transformation process. The term "growing" or "regeneration" as used herein means growing a plant from a protoplast, a plant cell, a group of plant cells, a plant part (including seeds), or a plant piece (e.g., from a protoplast, callus, or tissue part).

In vegetatively propagated crops, the mature transgenic plants are propagated by the taking of cuttings or by tissue culture techniques to produce multiple identical plants. Selection of desirable transformed plants is made and new varieties are obtained and propagated vegetatively for commercial use.

In seed-propagated crops, the mature transgenic plants can be self crossed to produce a homozygous inbred plant. The inbred plant produces seed containing the newly introduced polynucleotide fragment, preferably, heterologous polynucleotide fragment. These seeds can be grown to produce plants that would produce the selected phenotype, modified timing of flowering.

Parts obtained from the regenerated plant, such as flowers, seeds, leaves, branches, fruit, and the like are included in the invention, provided that these parts comprise cells that have been transformed as described. Progeny and variants, and mutants of the regenerated plants are also included within the scope of the invention, provided that these parts comprise the introduced polynucleotide fragments.

Plants exhibiting modified timing of flowering can be selected by visual observation. Commercially important crop plants have been bred for desirable characteristics, including uniformity in the time the plants are ready for harvesting. This has resulted in a high degree of uniformity in the number of leaves present on each plant in a population of plants grown under the same conditions. Due to the uniformity in the number of leaves present, alterations in the time of flower initiation can often be measured as a function of the number of leaves on a plant. For instance, if flower initiation is activated early in a plant, that plant will have fewer leaves relative to the same type of (or unmodified) plant grown under the same conditions that does not activate flower initiation early. Moreover, a plant that activates flower initiation early can also be said to have a shortened vegetative phase relative to the same type of plant grown under the same conditions that does not activate flower initiation early. Likewise, if flower initiation is repressed such that the plant undergoes flower initiation later, that plant will have more leaves relative to the same type of plant grown under the same conditions that does not repress flower initiation until later. Moreover, a plant that represses flower initiation may also be said to have a prolonged vegetative phase relative to the same type of plant grown under the same conditions that does not repress flower initiation. Alterations in the time of flower initiation can also be measured as a function of time.

The above disclosure generally describes the present invention. A more complete understanding can be obtained by reference to the following specific examples which are provided herein for purposes of illustration only and are not intended to limit the scope of the invention.

While the examples set forth below are executed in *Arabidopsis,* due to the simplicity in the genetic manipulation of that plant, the same techniques will work in other plants species. In fact, the high degree of sequence identity across plant species suggests that an FPA gene from one plant species will function, as a general rule, in other plants species.

EXAMPLES

Isolation of the FPA Gene

The FPA gene was isolated by positional cloning performed on fpa mutants of the Columbia ecotype of *Arabidopsis.* Unlike the Columbia ecotype, which flowers after producing 10–12 vegetative leaves, mutants which have lost FPA function flowered after producing 80–90 vegetative leaves.

Loss of function fpa alleles were created by both ethylmethanesulfonate (EMS:fpa-1, fpa-2, and fpa-4), and by Agrobacterium-mediated transfer DNA (T-DNA) mutagenesis (fpa-3, fpa-5, and fpa-6). The fpa-4 allele was determined to be a deletion of a 35 kb sequence which eliminated FPA function. This deletion was contained in the BAC 1O24 and sequenced by TIGR.

BAC 1024 was then used to generate a library of small clones containing 5–15 kb of DNA. These small clones were then transformed into fpa-3 via Agrobacterium-mediated transformation to determine the region in the plant genome that contained the FPA gene.

Several independent transformants were observed to rescue the fpa mutant phenotype (Table 1). The rescuing clones were then sequenced and it was discovered that all of the rescuing clones contained the same region of DNA. Analysis of this data further indicated that FPA was an RNA-binding protein, as indicated in SEQ ID No. 3.

TABLE 1

| Arabidopsis line | Rosette leaf number at flowering |
| --- | --- |
| Columbia (wild-type) | 10–12 |
| fpa mutant (Columbia) | 80–90 |
| fpa-3 (WS) | 50–65 |
| Wild-Type (WS) | 7–8 |
| fpa-3 + rescue clone 1 | 6–7 |
| fpa-3 + rescue clone 2 | 7–8 |
| fpa-3 + rescue clone 4 | 7–8 |

Additional fpa alleles were then analyzed. One allele (fpa-3) was found to contain a deletion that removed 2.5 kb of a promoter and 5' FPA coding region. The other two fpa-5, and fpa-6) alleles were found to contain T-DNA insertions in the FPA coding region. Two other independent fpa alleles (fpa-1 and fpa-2) which were generated by EMS mutagenesis were also sequenced. Both of these alleles contained DNA base changes in the RNA-binding protein that resulted in stop codons which truncated the FPA protein.

Overexpression of FPA Results in Altered Floral Induction

Expression using several different constructs containing partial or full-length FPA sequences yielded plants that had altered flowering times compared to that of non-transformed control plants. FPA has been used to generate both early and late-flowering phenotypes in transgenic *Arabidopsis*. This data implies that FPA is a potent regulator of floral induction and can either compensate for and/or bypass other blocks to floral induction. Due to the ability of FPA to produce altered flowering in many different genetic backgrounds and physiologic growth conditions it is anticipated that FPA will be able to regulate flowering in species other than *Arabidopsis*.

Early Flowering in Short Days Due to Expression of the Full-Length FPA Gene

The wild-type summer-annual WS accession of *Arabidopsis* was transformed with constructs containing the entire FPA gene using Agrobacterium-mediated transformation. The construct was prepared using the isolated FPA gene (amplified from genomic *Arabidopsis* DNA using the primers ATGGCGTTATCTATGAAGCCATTCAGAGCC (SEQ ID NO:7) and TCAAGGCCCCTGTCCAGCCGGAGTACC (SEQ ID NO:8)), and a 35S CaMV promoter. Sucessful transformants were then collected and grown in conditions to allow assessment of the FPA overexpression of flowering time.

To assay for altered flowering time, transformants were grown in both long day, and short day conditions. Overexpression caused early flowering in short day conditions (Table 2), as typical wild-type *Arabidopsis* strains generally flower after producing 25–30 leaves in short days.

TABLE 2

| Arabidopsis line | Rosette leaf number at time of flowering |
| --- | --- |
| WS (wild type) in Long days | 7–8 |
| WS + 35S::FPA in Long days | 6–9 |
| WS (wild type) in Short days | 25–30 |
| WS + 35S::FPA in Short days | 7–8* and 25–30* |

*Two types of plants were observed in SD: early flowering and wild-type flowering. Approximately %40 were of the early-flowering phenotype.

Generation of Early-Flowering Plants from Late-Flowering Genetic Backgrounds by Overexpression of FPA The FPA overexpression construct described in the generation of early-flowering plants in short days was used to investigate the ability of FPA to promote flowering in several genetic backgrounds that are later flowering than the WS accession. The effects of overexpression of FPA was determined in the following genetic backgrounds: fve-2 mutant, fca-1 mutant, and the naturally occurring dominant FRIGIDA (FRI)/FLC gene pair background. The results verify that FPA reduces the flowering time in the late-flowering plants to that of their respective wild-type plants (Table 3).

TABLE 3

| Genetic Background | Rosette leaf number at time of flowering in Long Days |
| --- | --- |
| Ler (wild-type) | 7–8 |
| Ler fve-2 | 18–22 |
| Ler fve-2 + 35S::FPA | 7–8 |
| Ler fca-1 | 20–24 |
| Ler fca-1 + 35S::FPA | 7–8 |
| Columbia (wild-type) | 10–12 |
| Columbia + FRI/FLC | 70–90 |
| Columbia + FRI/FLC + 35S::FPA | 10–12 |

The Generation of Late-Flowering *Arabidopsis* using FPA

Using the FPA polynucleotide sequence (SEQ ID NO:2), late-flowering *Arabidopsis* were generated using both anti-sense and cosuppression transgenes. An antisense construct was generated using the 5' coding region of FPA (amplified by the primers 5'. AAGACTTTAAAGGAGATGTTCAGCC (SEQ ID NO:9) and 5' CCTTTCCCATAGGTACACAAC-GAGC (SEQ ID NO:10)) and expressing the opposite strand under control of the CaMV 35S promoter. Primary transformants that displayed delayed flowering were selected and progeny were replanted. Upon replanting, late-flowering plants that phenocopied fpa mutants were isolated (i.e., flowered after producing 60 leaves).

Late-flowering *Arabidopsis* were likewise generated through cosuppression of fpa by overexpressing portions of the FPA polynucleotide sequence in the sense orientation with the 35S promoter. This approach also resulted in plants with delayed flowering that phenocopied fpa mutants (Table 4). Several constructs were able to produce late-flowering plants due to cosuppression. For example, constructs designed for overexpression of the full length EPA coding sequence and overexpression of partial fragments contained within the full-length FPA construct were able to generate late-flowering cosuppression phenotypes. Because little is known of the mechanism of cosuppression it was difficult to predict what features of a gene were advantageous for producing cossuppression. However, expression of either partial or full-length coding regions of FPA was sufficient to produce late-flowering plants through cosuppression mechanisms.

| Genetic background | Rosette leaf number at time of flowering in Long Days |
|---|---|
| Columbia (wild-type) | 10–12 |
| Columbia + FPA cosuppression construct | 55–80 |

Overexpression of FPA decreases FLC mRNA

The FLC gene is a central floral repressor that is responsible for delaying flowering in many species. To further investigate the role of FPA in causing early flowering in this background, FLC messenger RNA was quantified by RT-PCR (reverse-transcription based polymerase chain reaction). In the control plants that did not contain overexpressed FPA, there was substantial FLC message detected (Table 5). However, in the early-flowering 35S::FPA-containing plants there was no detectable FLC message, indicating that the overexpression of FPA in an FLC-expressing late-flowering background results in the removal of FLC message, and early flowering. (See, Table 3.) Accordingly, the introduction of 35S.-:FPA into a plant expressing FLC message provides a system to selectively remove FLC message from that plant.

TABLE 5

| Arabidopsis Genetic Background | FLC messenger RNA amount |
|---|---|
| Columbia + FRI/FLC | +++ |
| Columbia + FRI/FLC + 35S::FPA | none detectable |

We claim:

1. A transgenic plant comprising in its genome a transgene comprising a FPA polynucleotide sequence in sense orientation, wherein the FPA polynucleotide encodes a protein comprising SEQ ID NO:3, wherein expression of the transgene is sufficient to cause the plant to flower earlier as compared to other plants of the same species without the transgene.

2. The transgenic plant of claim 1, wherein the FPA polynucleotide sequence is from *Arabidopsis thaliana*.

3. A transgenic plant comprising in its genome a transgene comprising a FPA polynucleotide sequence in sense orientation, wherein expression of the transgene causes the plant to have an earlier flowering time as compared to non-transgenic plants of the same species, wherein the FPA polynucleotide sequence is SEQ ID NO:2.

4. Seed of the transgenic plant of claim 1 which carries the transgene in its genome.

5. A plant grown from the seed of claim 4 which carries the transgene in its genome.

6. A plant comprising in its genome a genetic construct comprising an isolated FPA polynucleotide sequence in sense orientation, wherein expression of the sequence in the plant causes an earlier flowering time of the plant as compared to non-transgenic plants of the same species, wherein the FPA polynucleotide is SEQ ID NO:2.

7. The plant of claim 6, wherein the genetic construct further comprises a promoter, not natively associated with the FPA polynucleotide sequence, which promotes the expression of the EPA polynucleotide sequence in the plant.

8. The plant of claim 6, wherein the EPA polynucleotide sequence is from *Arabidopsis thaliana*.

9. A seed of the plant of claim 6 which carries the genetic construct in its genome.

10. A plant grown from the seed of claim 9 which carries the genetic construct in its genome.

11. A plant seed comprising in its genome a genetic construct comprising an isolated FPA polynucleotide sequence operably linked to a plant expressible promoter in sense orientation, wherein the FPA polynucleotide encodes a protein comprising SEQ ID NO:3, and wherein expression of the sequence in the plant causes an earlier flowering time of the plant as compared to non-transgenic plants of the same species.

12. The seed of claim 11, wherein the FPA polynucleotide sequence is from *Arabidopsis thaliana*.

13. A transgenic plant cultivated from the seed of claim 11, wherein the plant comprises the genetic construct.

14. An isolated DNA sequence comprising the coding sequence for a FPA gene from *Arabidopsis thaliana*, the FPA gene having a polynucleotide sequence of SEQ ID NO:2.

15. An isolated DNA molecule comprising a DNA sequence encoding the FPA protein from *Arabidopsis thaliana*, wherein the protein comprises SEQ ID NO:3.

16. The DNA sequence of claim 15, wherein the DNA sequence is SEQ ID NO:2.

17. A method of producing a transgenic plant with an earlier flowering time comprising: constructing a genetic construct comprising a plant expressible promoter operably linked to an FPA polynucleotide sequence in sense orientation, wherein the FPA polynucleotide comprises a coding region that encodes a protein comprising SEQ ID NO:3, introducing the genetic construct into a plant cell, regenerating a plant from the plant cell, selecting a plant comprising the genetic construct, and growing the plant under conditions that allow expression of the FPA gene such that the plant flowers earlier than plants of the same species without the genetic construct.

* * * * *

SEQUENCE LISTING

<160> NUMBER OF SEQ ID NOS: 6

<210> SEQ ID NO 1
<211> LENGTH: 4593
<212> TYPE: DNA
<213> ORGANISM: Arabidopsis thaliana

<400> SEQUENCE: 1

```
atggcgttat ctatgaagcc attcagagcc gatgattccg gtttccagtc aaacaatctt      60
tgggtcggta gcctaacgcc ggagacgaca gagtcagatc tgaccgagtt gtttggaaga     120
tacggcgata ttgatagaat cacggtgtat tcttcacgag gctttgcgtt tatatactac     180
agacatgtgg aggaagcagt cgcagccaaa gaggctcttc aaggagcaaa tttgaatgga     240
agtcaaatta agatcgaata cgcacgaccg gtttgttctt atctatatct tcgtttgttc     300
tctaactttg attgtctttt gtcaacgatt atactctttt tgcgaattca tagtccaggt     360
tcacaaaact ttgatgatgc ttgtttagtc caaaaatttc ttgttgaatc tgttttttt      420 ttcctcatcg tacaaatcaa agtcgaaacc tagttttttt ctattatacg tcgttagctt     480
aaggcgaaac ctgatccgat cgaaacgtct tttctcaaat tactttggtt atatcgaact     540
cgcgcaaagc caaccacag agaagctctg caaaatttga tgttaaagca tatataactc      600
ttagcgaatg agctctgcaa aagaatacat caaacacatg tttactctcg tttatgcgaa     660
gaaggtttaa tccgattgtc gtttatctgc aaacttgtat ccgcgtttag cagtctgatt     720
tcaggttcgc ttcagatgtt aaatctcaca agcttgagta tgaatgtatt gcgtactcca     780
ctcgaaattc gcaatggtga aaatttggaa gcgagcaaac tctatcatcg gccaaacaga     840
taagaaattt tggagtttaa aagttcagtt tcctgcaaaa atcaaaccgc gtggagaaat     900
ttgtctatgg cggtacgtag atatcaataa ctgcatctgc gaaacagaaa attctggcaa     960
ccgtatcgtc ctaactccta gtatcgctgg cacatatcca tatcagtgtg agggagtttt    1020
gggcttgttt tggctcgatg cttcaggaag acaaattacg tggttgttaa ggcggctaac    1080
tctaccaatc agaaacgctt tattcgaaga accatgtttg ttcctcaatt cccatcccta    1140
cgtacaatct gggctttccc attgtagttc cttaggaagt tgacttcttc acaaccattc    1200
tgggattggt acagttgcag tggacaagac aaatattcat ttgcaggcag actcaaattt    1260
caatgtcttg ccggctttga gtacttaaat ggagtgttca gggattggtt tatttgggac    1320
```

-continued

```
tcaggcaatg gataaagaca ggaatgtttt gcagaaagta ttaatgtctt tccggctttg    1380
gggactacat acttctccta cagacaaaat ctgatgttta ggcaagagaa actattaaca    1440
ctgatttaat agagaaagag gagatggttt ctccttgcgg caattttatt tgtttaggaa    1500
agcaattgat atgaattggt gtcgtagtgt agttgaaatt actagttagt ttgtgtgttt    1560
agtttccttg atgtttgatg ctttattctt ggcaacctat ctgggtagta tcgccttctt    1620
atcgaccttt tcttgttgca ggcaaaacct tgtaagagtc tatgggtggg tggaatcggc    1680
cctaatgtct ccaaggatga cctggaggaa gagttcagca agtttgggaa aatcgaggat    1740
tttaggtttc tcagagaacg caagacagct ttcattgatt attatgagat ggatgatgct    1800
ttacaggcta agagcatgaa tggaaagcct atgggtggta gcttttgcg tgttgatttt    1860 ctccggtcac aagcgccaaa aaagtaagc actcttgtgg catttgattt ttactttga     1920 aaacgctcca gtaaacattt tgtttagttt cataatttgc gtcaaactga tagggctgag    1980
ctctgtcttg tgccctagg agcagtattt actcgtctct atttcattgt agagtaggct    2040
caacttctta agtctgaaat caagttacct tgtgttatc ttcaggaaca atgggctggc     2100
tcttacgata acagaaatgg caatatgaat cataaaccgc aggttagtct tgaatgttga    2160
aagtatgtct cttgttacta gtgatatgta taggttactg gttttgacgt tttgttatat    2220
tcttacagta tcctcactca tatgaagact ttaaaggaga tgtccagcca agtaaggttc    2280
tgtggattgg gttccctcct actgctacac aatgcaatga tgagcaaatt ctgcacaatg    2340
cgatgatact ctttggtgag atcgagaggg taaaaagtta cccatcaagg aattttgcac    2400
ttgtggagtt taggagcgcg gaggaagctc gccaatgcaa ggaaggccta caggggaggt    2460
tattcaataa tcctagaatc aaaattatgt actcaaacga tgagttgcct cctgagcaag    2520
acgatactag tttttactct ggtatgaaac ggtcaaggac agatatgttc aataatgatc    2580
cttcatttgt atcttctcct cattctactg gaattcctgg gtctatgagg cccctcagag    2640
gtacaaatga gcgttcatat aatggtgcag aatacaatga cgttgttggt aaggagccaa    2700
actggaggag gccatctgca aatgaactg gaatactccc atctccaaca ggacctggaa     2760
tcctcccatc tcctgcacaa ggtacgaggc gccctatgag gtcaaacccc gattcttggg    2820
aaggatatga tcctgctcag ttggtcagag aaagtaaacg aaccagaaga gatggatcag    2880
tggacggttt tactccaatg ggtgtcgatg agaggtcatt tggtcgaggt tcagttgctg    2940
ctagacctat ccgtggcccc cctgattctg atcacatatg gagaggaatg attgccaagg    3000
gtggaactcc cgtctgttgt gctcgttgtg tacctatggg aaagggggatt gaaactaaac    3060 tgtgagtact aatttctagc actttaaccc ttctagtgtt ttcttttca gagcgattta    3120 tatattttcc atttcattct cgatggaagt aacattatta tagatagtac attttttattt   3180 tactattact tgtttagttt ctgagatgtc ttgattttca tggtgttgat tcattttgg     3240 cattgccctc aattactgac tttgttttt ttttaataat tgatttatag gcctgaggtc      3300
gtcaattgtt cagcaagaac tgatttgaat atgctcgcta acattacgc cgttgccatt      3360 ggatgtgaga tcgttttttt cgtaccagac agggaagaag attttgcgtc ttacactgaa    3420
tttctccggt accttagctc aaaagatcgg gcgggtgttg ccaaattaga tgatggtaca    3480 acttattct tggtgcctcc atcagatttc ttaactgatg tactccaagt gacccgtcaa      3540
gaacggctat atggtgttgt tctcaagtta ccccgccag ccgttcctgt tacagcatca      3600
tacagacaag aatctcagtc caatcctctg cattatatgg atcaagcccg ggattcacct    3660
gccaatgcta gtcacagttt atatcctcct agggaaaatt acattagggg tgcaccagaa    3720
```

-continued

```
catttgacag ctgcttcaaa accatctgtt agcgagcctc tcagaatacc taataatgca    3780
gcgcctcaag ctggggttag tttaactccg gagcttttag ccactctggc atctattctc    3840
cctgcaactt ctcaacctgc tgcccctgag agtcaccaac ctatgtcagg accttcaaca    3900
gttgtttcca cagcacatca gtccaatgga ctgtacaatg gagaagcacc gtctcaagct    3960
tggaaaagag gtccacaaac agttcatgat gcgtcaaatc agtcattcca acaatacgga    4020
aatcagtaca ctccagctgg gcaactacct cctcctcctt cgcgttaccc tccagcttca    4080
aacaacccca actacactag tggaatggtc catggcaaca tgcaatacca gagccaatct    4140
gttaacatgc ctcagctgtc tccgttacca aatatgcctc ataataatta ttccatgtac    4200
actcagggtt cgtcaaatca tcctgttttct cagcccatgg tccagcaata ccaaccagaa    4260
gcgtccatgc caaaccaaaa ctatggtcca attccaagtt atcagcaagc taattttcat    4320
ggcgtaacaa caaatcaggc acagaactta acccttccc aatttcaagc tgccatgcaa    4380
ccaccagcag ataaggcaaa tttagagcca caaaaccaag cactacgatt gcagcctatg    4440
atctctgggg atggtcaggg tacaacagat ggggaggtcg ataagaatca gagataccag    4500
tcaacactac aatttgcagc aaaccttctt ctccagatac agcagaaaca gcagcaacag    4560
tcttcaggta ctccggctgg acaggggcct tga                                 4593
```

<210> SEQ ID NO 2
<211> LENGTH: 2706
<212> TYPE: DNA
<213> ORGANISM: Arabidopsis thaliana
<220> FEATURE:
<221> NAME/KEY: CDS
<222> LOCATION: (1)..(2706)
<221> NAME/KEY: misc_binding
<222> LOCATION: (46)..(279)
<223> OTHER INFORMATION: RNA Binding Region
<221> NAME/KEY: misc_binding
<222> LOCATION: (283)..(522)
<223> OTHER INFORMATION: RNA Binding Region
<221> NAME/KEY: misc_binding
<222> LOCATION: (610)..(852)
<223> OTHER INFORMATION: RNA Binding Region

<400> SEQUENCE: 2

```
atg gcg tta tct atg aag cca ttc aga gcc gat gat tcc ggt ttc cag           48
Met Ala Leu Ser Met Lys Pro Phe Arg Ala Asp Asp Ser Gly Phe Gln
 1               5                  10                  15 tca aac aat ctt tgg gtc ggt agc cta acg ccg gag acg aca gag tca           96
Ser Asn Asn Leu Trp Val Gly Ser Leu Thr Pro Glu Thr Thr Glu Ser
             20                  25                  30 gat ctg acc gag ttg ttt gga aga tac ggc gat att gat aga atc acg          144
Asp Leu Thr Glu Leu Phe Gly Arg Tyr Gly Asp Ile Asp Arg Ile Thr
         35                  40                  45 gtg tat tct tca cga ggc ttt gcg ttt ata tac tac aga cat gtg gag          192
Val Tyr Ser Ser Arg Gly Phe Ala Phe Ile Tyr Tyr Arg His Val Glu
     50                  55                  60 gaa gca gtc gca gcc aaa gag gct ctt caa gga gca aat ttg aat gga          240
Glu Ala Val Ala Ala Lys Glu Ala Leu Gln Gly Ala Asn Leu Asn Gly
 65                  70                  75                  80 agt caa att aag atc gaa tac gca cga ccg gca aaa cct tgt aag agt          288
Ser Gln Ile Lys Ile Glu Tyr Ala Arg Pro Ala Lys Pro Cys Lys Ser
                 85                  90                  95 cta tgg gtg ggt gga atc ggc cct aat gtc tcc aag gat gac ctg gag          336
Leu Trp Val Gly Gly Ile Gly Pro Asn Val Ser Lys Asp Asp Leu Glu
            100                 105                 110
```

```
gaa gag ttc agc aag ttt ggg aaa atc gag gat ttt agg ttt ctc aga      384
Glu Glu Phe Ser Lys Phe Gly Lys Ile Glu Asp Phe Arg Phe Leu Arg
            115                 120                 125 gaa cgc aag aca gct ttc att gat tat tat gag atg gat gat gct tta      432
Glu Arg Lys Thr Ala Phe Ile Asp Tyr Tyr Glu Met Asp Asp Ala Leu
        130                 135                 140 cag gct aag agc atg aat gga aag cct atg ggt ggt agc ttt ttg cgt      480
Gln Ala Lys Ser Met Asn Gly Lys Pro Met Gly Gly Ser Phe Leu Arg
145                 150                 155                 160 gtt gat ttt ctc cgg tca caa gcg cca aaa aaa gaa caa tgg gct ggc      528
Val Asp Phe Leu Arg Ser Gln Ala Pro Lys Lys Glu Gln Trp Ala Gly
                165                 170                 175 tct tac gat aac aga aat ggc aat atg aat cat aaa ccg cag tat cct      576
Ser Tyr Asp Asn Arg Asn Gly Asn Met Asn His Lys Pro Gln Tyr Pro
            180                 185                 190 cac tca tat gaa gac ttt aaa gga gat gtc cag cca agt aag gtt ctg      624
His Ser Tyr Glu Asp Phe Lys Gly Asp Val Gln Pro Ser Lys Val Leu
        195                 200                 205 tgg att ggg ttc cct cct act gct aca caa tgc aat gat gag caa att      672
Trp Ile Gly Phe Pro Pro Thr Ala Thr Gln Cys Asn Asp Glu Gln Ile
    210                 215                 220 ctg cac aat gcg atg ata ctc ttt ggt gag atc gag agg gta aaa agt      720
Leu His Asn Ala Met Ile Leu Phe Gly Glu Ile Glu Arg Val Lys Ser
225                 230                 235                 240 tac cca tca agg aat ttt gca ctt gtg gag ttt agg agc gcg gag gaa      768
Tyr Pro Ser Arg Asn Phe Ala Leu Val Glu Phe Arg Ser Ala Glu Glu
                245                 250                 255 gct cgc caa tgc aag gaa ggc cta cag ggg agg tta ttc aat aat cct      816
Ala Arg Gln Cys Lys Glu Gly Leu Gln Gly Arg Leu Phe Asn Asn Pro
            260                 265                 270 aga atc aaa att atg tac tca aac gat gag ttg cct cct gag caa gac      864
Arg Ile Lys Ile Met Tyr Ser Asn Asp Glu Leu Pro Pro Glu Gln Asp
        275                 280                 285 gat act agt ttt tac tct ggt atg aaa cgg tca agg aca gat atg ttc      912
Asp Thr Ser Phe Tyr Ser Gly Met Lys Arg Ser Arg Thr Asp Met Phe
290                 295                 300 aat aat gat cct tca tgt gta tct tct cct cat tct act gga att cct      960
Asn Asn Asp Pro Ser Cys Val Ser Ser Pro His Ser Thr Gly Ile Pro
305                 310                 315                 320 ggg tct atg agg ccc ctc aga ggt acg aat gag cgt tca tat aat ggt     1008
Gly Ser Met Arg Pro Leu Arg Gly Thr Asn Glu Arg Ser Tyr Asn Gly
                325                 330                 335 gca gaa tac aat gac gtt gtt ggt aag gag cca aac tgg agg agg cca     1056
Ala Glu Tyr Asn Asp Val Val Gly Lys Glu Pro Asn Trp Arg Arg Pro
            340                 345                 350 tct gca aat gga act gga ata ctc cca tct cca aca gga cct gga atc     1104
Ser Ala Asn Gly Thr Gly Ile Leu Pro Ser Pro Thr Gly Pro Gly Ile
        355                 360                 365 ctc cca tct cct gca caa ggt acg agg cgc cct atg agg tca aac ccc     1152
Leu Pro Ser Pro Ala Gln Gly Thr Arg Arg Pro Met Arg Ser Asn Pro
370                 375                 380 gat tct tgg gaa gga tat gat cct gct cag ttg gtc aga gaa agt aaa     1200
Asp Ser Trp Glu Gly Tyr Asp Pro Ala Gln Leu Val Arg Glu Ser Lys
385                 390                 395                 400 cga acc aga aga gat gga tca gtg gac ggt ttt act cca atg ggt gtc     1248
Arg Thr Arg Arg Asp Gly Ser Val Asp Gly Phe Thr Pro Met Gly Val
                405                 410                 415 gat gag agg tca ttt ggt cga ggt tca gtt gct gct aga cct atc cgt     1296
Asp Glu Arg Ser Phe Gly Arg Gly Ser Val Ala Ala Arg Pro Ile Arg
            420                 425                 430
```

-continued

| | | |
|---|---|---|
| ggc ccc cct gat tct gat cac ata tgg aga gga atg att gcc aag ggt<br>Gly Pro Pro Asp Ser Asp His Ile Trp Arg Gly Met Ile Ala Lys Gly<br>435 440 445 | | 1344 |
| gga act ccc gtc tgt tgt gct cgt tgt gta cct atg gga aag ggg att<br>Gly Thr Pro Val Cys Cys Ala Arg Cys Val Pro Met Gly Lys Gly Ile<br>450 455 460 | | 1392 |
| gaa act aaa ctg cct gag gtc gtc aat tgt tca gca aga act gat ttg<br>Glu Thr Lys Leu Pro Glu Val Val Asn Cys Ser Ala Arg Thr Asp Leu<br>465 470 475 480 | | 1440 |
| aat atg ctc gct aaa cat tac gcc gtt gcc att gga tgt gag atc gtt<br>Asn Met Leu Ala Lys His Tyr Ala Val Ala Ile Gly Cys Glu Ile Val<br>485 490 495 | | 1488 |
| ttt ttc gta cca gac agg gaa gaa gat ttt gcg tct tac act gaa ttt<br>Phe Phe Val Pro Asp Arg Glu Glu Asp Phe Ala Ser Tyr Thr Glu Phe<br>500 505 510 | | 1536 |
| ctc cgg tac ctt agc tca aaa gat cgg gcg ggt gtt gcc aaa tta gat<br>Leu Arg Tyr Leu Ser Ser Lys Asp Arg Ala Gly Val Ala Lys Leu Asp<br>515 520 525 | | 1584 |
| gat ggt aca act tta ttc ttg gtg cct cca tca gat ttc tta act gat<br>Asp Gly Thr Thr Leu Phe Leu Val Pro Pro Ser Asp Phe Leu Thr Asp<br>530 535 540 | | 1632 |
| gta ctc caa gtg acc cgt caa gaa cgg cta tat ggt gtt gtt ctc aag<br>Val Leu Gln Val Thr Arg Gln Glu Arg Leu Tyr Gly Val Val Leu Lys<br>545 550 555 560 | | 1680 |
| tta ccc ccg cca gcc gtt cct gtt aca gca tca tac aga caa gaa tct<br>Leu Pro Pro Pro Ala Val Pro Val Thr Ala Ser Tyr Arg Gln Glu Ser<br>565 570 575 | | 1728 |
| cag tcc aat cct ctg cat tat atg gat caa gcc cgg gat tca cct gcc<br>Gln Ser Asn Pro Leu His Tyr Met Asp Gln Ala Arg Asp Ser Pro Ala<br>580 585 590 | | 1776 |
| aat gct agt cac agt tta tat cct cct agg gaa aat tac att agg ggt<br>Asn Ala Ser His Ser Leu Tyr Pro Pro Arg Glu Asn Tyr Ile Arg Gly<br>595 600 605 | | 1824 |
| gca cca gaa cat ttg aca gct gct tca aaa cca tct gtt agc gag cct<br>Ala Pro Glu His Leu Thr Ala Ala Ser Lys Pro Ser Val Ser Glu Pro<br>610 615 620 | | 1872 |
| ctc aga ata cct aat aat gca gcg cct caa gct ggg gtt agt tta act<br>Leu Arg Ile Pro Asn Asn Ala Ala Pro Gln Ala Gly Val Ser Leu Thr<br>625 630 635 640 | | 1920 |
| ccg gag ctt tta gcc act ctg gca tct att ctc cct gca act tct caa<br>Pro Glu Leu Leu Ala Thr Leu Ala Ser Ile Leu Pro Ala Thr Ser Gln<br>645 650 655 | | 1968 |
| cct gct gcc cct gag agt cac caa cct atg tca gga cct tca aca gtt<br>Pro Ala Ala Pro Glu Ser His Gln Pro Met Ser Gly Pro Ser Thr Val<br>660 665 670 | | 2016 |
| gtt tcc aca gca cat cag tcc aat gga ctg tac aat gga gaa gca ccg<br>Val Ser Thr Ala His Gln Ser Asn Gly Leu Tyr Asn Gly Glu Ala Pro<br>675 680 685 | | 2064 |
| tct caa gct tgg aaa aga ggt cca caa aca gtt cat gat gcg tca aat<br>Ser Gln Ala Trp Lys Arg Gly Pro Gln Thr Val His Asp Ala Ser Asn<br>690 695 700 | | 2112 |
| cag tca ttc caa caa tac gga aat cag tac act cca gct ggg caa cta<br>Gln Ser Phe Gln Gln Tyr Gly Asn Gln Tyr Thr Pro Ala Gly Gln Leu<br>705 710 715 720 | | 2160 |
| cct cct cct cct tcg cgt tac cct cca gct tca aac aac ccc aac tac<br>Pro Pro Pro Pro Ser Arg Tyr Pro Pro Ala Ser Asn Asn Pro Asn Tyr<br>725 730 735 | | 2208 |
| act agt gga atg gtc cat ggc aac atg caa tac cag agc caa tct gtt<br>Thr Ser Gly Met Val His Gly Asn Met Gln Tyr Gln Ser Gln Ser Val | | 2256 |

```
                    740             745              750
aac atg cct cag ctg tct ccg tta cca aat atg cct cat aat aat tat    2304
Asn Met Pro Gln Leu Ser Pro Leu Pro Asn Met Pro His Asn Asn Tyr
        755             760              765 tcc atg tac act cag ggt tcg tca aat cat cct gtt tct cag ccc atg    2352
Ser Met Tyr Thr Gln Gly Ser Ser Asn His Pro Val Ser Gln Pro Met
770             775             780 gtc cag caa tac caa cca gaa gcg tcc atg cca aac caa aac tat ggt    2400
Val Gln Gln Tyr Gln Pro Glu Ala Ser Met Pro Asn Gln Asn Tyr Gly
785             790             795             800 cca att cca agt tat cag caa gct aat ttt cat ggc gta aca aca aat    2448
Pro Ile Pro Ser Tyr Gln Gln Ala Asn Phe His Gly Val Thr Thr Asn
        805             810             815 cag gca cag aac tta aac cct tcc caa ttt caa gct gcc atg caa cca    2496
Gln Ala Gln Asn Leu Asn Pro Ser Gln Phe Gln Ala Ala Met Gln Pro
            820             825             830 cca gca gat aag gca aat tta gag cca caa aac caa gca cta cga ttg    2544
Pro Ala Asp Lys Ala Asn Leu Glu Pro Gln Asn Gln Ala Leu Arg Leu
        835             840             845 cag cct atg atc tct ggg gat ggt cag ggt aca aca gat ggg gag gtc    2592
Gln Pro Met Ile Ser Gly Asp Gly Gln Gly Thr Thr Asp Gly Glu Val
850             855             860 gat aag aat cag aga tac cag tca aca cta caa ttt gca gca aac ctt    2640
Asp Lys Asn Gln Arg Tyr Gln Ser Thr Leu Gln Phe Ala Ala Asn Leu
865             870             875             880 ctt ctc cag ata cag cag aaa cag cag caa cag tct tca ggt act ccg    2688
Leu Leu Gln Ile Gln Gln Lys Gln Gln Gln Gln Ser Ser Gly Thr Pro
        885             890             895 gct gga cag ggg cct tga                                            2706
Ala Gly Gln Gly Pro
            900

<210> SEQ ID NO 3
<211> LENGTH: 901
<212> TYPE: PRT
<213> ORGANISM: Arabidopsis thaliana

<400> SEQUENCE: 3

Met Ala Leu Ser Met Lys Pro Phe Arg Ala Asp Asp Ser Gly Phe Gln
1               5                   10                  15

Ser Asn Asn Leu Trp Val Gly Ser Leu Thr Pro Glu Thr Thr Glu Ser
            20                  25                  30

Asp Leu Thr Glu Leu Phe Gly Arg Tyr Gly Asp Ile Asp Arg Ile Thr
        35                  40                  45

Val Tyr Ser Ser Arg Gly Phe Ala Phe Ile Tyr Tyr Arg His Val Glu
    50                  55                  60

Glu Ala Val Ala Ala Lys Glu Ala Leu Gln Gly Ala Asn Leu Asn Gly
65                  70                  75                  80

Ser Gln Ile Lys Ile Glu Tyr Ala Arg Pro Ala Lys Pro Cys Lys Ser
                85                  90                  95

Leu Trp Val Gly Gly Ile Gly Pro Asn Val Ser Lys Asp Leu Glu
            100                 105                 110

Glu Glu Phe Ser Lys Phe Gly Lys Ile Glu Asp Phe Arg Phe Leu Arg
        115                 120                 125

Glu Arg Lys Thr Ala Phe Ile Asp Tyr Tyr Glu Met Asp Asp Ala Leu
    130                 135                 140

Gln Ala Lys Ser Met Asn Gly Lys Pro Met Gly Gly Ser Phe Leu Arg
145                 150                 155                 160
```

```
Val Asp Phe Leu Arg Ser Gln Ala Pro Lys Lys Glu Gln Trp Ala Gly
            165                 170                 175

Ser Tyr Asp Asn Arg Asn Gly Asn Met Asn His Lys Pro Gln Tyr Pro
            180                 185                 190

His Ser Tyr Glu Asp Phe Lys Gly Asp Val Gln Pro Ser Lys Val Leu
            195                 200                 205

Trp Ile Gly Phe Pro Pro Thr Ala Thr Gln Cys Asn Asp Glu Gln Ile
    210                 215                 220

Leu His Asn Ala Met Ile Leu Phe Gly Glu Ile Glu Arg Val Lys Ser
225                 230                 235                 240

Tyr Pro Ser Arg Asn Phe Ala Leu Val Glu Phe Arg Ser Ala Glu Glu
            245                 250                 255

Ala Arg Gln Cys Lys Glu Gly Leu Gln Gly Arg Leu Phe Asn Asn Pro
            260                 265                 270

Arg Ile Lys Ile Met Tyr Ser Asn Asp Glu Leu Pro Pro Glu Gln Asp
            275                 280                 285

Asp Thr Ser Phe Tyr Ser Gly Met Lys Arg Ser Arg Thr Asp Met Phe
            290                 295                 300

Asn Asn Asp Pro Ser Cys Val Ser Ser Pro His Ser Thr Gly Ile Pro
305                 310                 315                 320

Gly Ser Met Arg Pro Leu Arg Gly Thr Asn Glu Arg Ser Tyr Asn Gly
            325                 330                 335

Ala Glu Tyr Asn Asp Val Val Gly Lys Glu Pro Asn Trp Arg Arg Pro
            340                 345                 350

Ser Ala Asn Gly Thr Gly Ile Leu Pro Ser Pro Thr Gly Pro Gly Ile
            355                 360                 365

Leu Pro Ser Pro Ala Gln Gly Thr Arg Arg Pro Met Arg Ser Asn Pro
            370                 375                 380

Asp Ser Trp Glu Gly Tyr Asp Pro Ala Gln Leu Val Arg Glu Ser Lys
385                 390                 395                 400

Arg Thr Arg Arg Asp Gly Ser Val Asp Gly Phe Thr Pro Met Gly Val
            405                 410                 415

Asp Glu Arg Ser Phe Gly Arg Gly Ser Val Ala Ala Arg Pro Ile Arg
            420                 425                 430

Gly Pro Pro Asp Ser Asp His Ile Trp Arg Gly Met Ile Ala Lys Gly
            435                 440                 445

Gly Thr Pro Val Cys Cys Ala Arg Cys Val Pro Met Gly Lys Gly Ile
            450                 455                 460

Glu Thr Lys Leu Pro Glu Val Val Asn Cys Ser Ala Arg Thr Asp Leu
465                 470                 475                 480

Asn Met Leu Ala Lys His Tyr Ala Val Ala Ile Gly Cys Glu Ile Val
            485                 490                 495

Phe Phe Val Pro Asp Arg Glu Glu Asp Phe Ala Ser Tyr Thr Glu Phe
            500                 505                 510

Leu Arg Tyr Leu Ser Ser Lys Asp Arg Ala Gly Val Ala Lys Leu Asp
            515                 520                 525

Asp Gly Thr Thr Leu Phe Leu Val Pro Pro Ser Asp Phe Leu Thr Asp
            530                 535                 540

Val Leu Gln Val Thr Arg Gln Glu Arg Leu Tyr Gly Val Val Leu Lys
545                 550                 555                 560

Leu Pro Pro Pro Ala Val Pro Val Thr Ala Ser Tyr Arg Gln Glu Ser
            565                 570                 575
```

-continued

| | | | | | | | | | | | | |
|---|---|---|---|---|---|---|---|---|---|---|---|---|
|Gln|Ser|Asn|Pro|Leu|His|Tyr|Met|Asp|Gln|Ala|Arg|Asp|Ser|Pro|Ala|
| | | |580| | | |585| | | |590| |

Asn Ala Ser His Ser Leu Tyr Pro Pro Arg Glu Asn Tyr Ile Arg Gly
            595                 600                 605

Ala Pro Glu His Leu Thr Ala Ala Ser Lys Pro Ser Val Ser Glu Pro
        610                 615                 620

Leu Arg Ile Pro Asn Asn Ala Ala Pro Gln Ala Gly Val Ser Leu Thr
625                 630                 635                 640

Pro Glu Leu Leu Ala Thr Leu Ala Ser Ile Leu Pro Ala Thr Ser Gln
            645                 650                 655

Pro Ala Ala Pro Glu Ser His Gln Pro Met Ser Gly Pro Ser Thr Val
                660                 665                 670

Val Ser Thr Ala His Gln Ser Asn Gly Leu Tyr Asn Gly Glu Ala Pro
            675                 680                 685

Ser Gln Ala Trp Lys Arg Gly Pro Gln Thr Val His Asp Ala Ser Asn
        690                 695                 700

Gln Ser Phe Gln Gln Tyr Gly Asn Gln Tyr Thr Pro Ala Gly Gln Leu
705                 710                 715                 720

Pro Pro Pro Pro Ser Arg Tyr Pro Pro Ala Ser Asn Asn Pro Asn Tyr
                725                 730                 735

Thr Ser Gly Met Val His Gly Asn Met Gln Tyr Gln Ser Gln Ser Val
            740                 745                 750

Asn Met Pro Gln Leu Ser Pro Leu Pro Asn Met Pro His Asn Asn Tyr
        755                 760                 765

Ser Met Tyr Thr Gln Gly Ser Ser Asn His Pro Val Ser Gln Pro Met
770                 775                 780

Val Gln Gln Tyr Gln Pro Glu Ala Ser Met Pro Asn Gln Asn Tyr Gly
785                 790                 795                 800

Pro Ile Pro Ser Tyr Gln Gln Ala Asn Phe His Gly Val Thr Thr Asn
            805                 810                 815

Gln Ala Gln Asn Leu Asn Pro Ser Gln Phe Gln Ala Ala Met Gln Pro
        820                 825                 830

Pro Ala Asp Lys Ala Asn Leu Glu Pro Gln Asn Gln Ala Leu Arg Leu
        835                 840                 845

Gln Pro Met Ile Ser Gly Asp Gly Gln Gly Thr Thr Asp Gly Glu Val
850                 855                 860

Asp Lys Asn Gln Arg Tyr Gln Ser Thr Leu Gln Phe Ala Ala Asn Leu
865                 870                 875                 880

Leu Leu Gln Ile Gln Gln Lys Gln Gln Gln Gln Ser Ser Gly Thr Pro
            885                 890                 895

Ala Gly Gln Gly Pro
            900

```
<210> SEQ ID NO 4
<211> LENGTH: 801
<212> TYPE: DNA
<213> ORGANISM: Arabidopsis thaliana
<220> FEATURE:
<223> OTHER INFORMATION: FPA antisense fragment

<400> SEQUENCE: 4
cctttcccat aggtacacaa cgagcacaac agacgggagt tccacccttg gcaatcattc      60
ctctccatat gtgatcagaa tcaggggggc acggatagg tctagcagca actgaacctc     120
gaccaaatga cctctcatcg acacccattg gagtaaaacc gtccactgat ccatctcttc     180
```

-continued

| | |
|---|---|
| tggttcgttt actttctctg accaactgag caggatcata tccttcccaa gaatcgggt | 240 |
| ttgacctcat agggcgcctc gtaccttgtg caggagatgg gaggattcca ggtcctgttg | 300 |
| gagatgggag tattccagtt ccatttgcag atggcctcct ccagtttggc tccttaccaa | 360 |
| caacgtcatt gtattctgca ccattatatg aacgctcatt tgtacctctg agggcctca | 420 |
| tagacccagg aattccagta gaatgaggag aagatacaaa tgaaggatca ttattgaaca | 480 |
| tatctgtcct tgaccgtttc ataccagagt aaaaactagt atcgtcttgc tcaggaggca | 540 |
| actcatcgtt tgagtacata attttgattc taggattatt gaataacctc ccctgtaggc | 600 |
| cttccttgca ttggcgagct tcctccgcgc tcctaaactc cacaagtgca aaattccttg | 660 |
| atgggtaact ttttacccctc tcgatctcac caaagagtat catcgcattg tgcagaattt | 720 |
| gctcatcatt gcattgtgta gcagtaggag ggaacccaat ccacagaacc ttacttggct | 780 |
| ggacatctcc tttaaagtct t | 801 |

<210> SEQ ID NO 5
<211> LENGTH: 349
<212> TYPE: DNA
<213> ORGANISM: Arabidopsis thaliana
<220> FEATURE:
<223> OTHER INFORMATION: Portion of FPA coding region

<400> SEQUENCE: 5

| | |
|---|---|
| atggcgttat ctatgaagcc attcagagcc gatgattccg gtttccagtc aaacaatctt | 60 |
| tgggtcggta gcctaacgcc ggagacgaca gagtcgagtc tgaccgagtt gtttggaaga | 120 |
| tacggcgata ttgatagaat cacggtgtat tcttcacgag gctttgcgtt tatatactac | 180 |
| agacatgtgg aggaagcagt cgcagccaaa gaggctcttc aaggagcaaa tttgaatgga | 240 |
| agtcaaatta agatcgaata cgcacgaccg gtttgttctt atctatatct tcgtttgttc | 300 |
| tctaactttg attgtctttt gtcaacgatt atactctttt tgcgaattc | 349 |

<210> SEQ ID NO 6
<211> LENGTH: 3715
<212> TYPE: DNA
<213> ORGANISM: Arabidopsis thaliana
<220> FEATURE:
<223> OTHER INFORMATION: FPA promoter plus intron

<400> SEQUENCE: 6

| | |
|---|---|
| tgagaagtct gatgcacaa tcattcaatc tactgcagat cagcttcttg gttgtgggaa | 60 |
| aggttagaac catctcgcta ttaacaatta taatgccttt ttgaagtgtt cttggctaag | 120 |
| tattcagttg tattgcttga agtccgcatc tcatctagct atggatatga tgatgcatgt | 180 |
| tcacaaggct taacctggaa agaatctatc tctatttttca acttagattt gtttgcttct | 240 |
| agatgtctag aacatgctga agtatctgct tggttaattt acatcttctt ccagtccatg | 300 |
| taatttcatg cgagttccaa ctttatttca tgcacatata acaaactca aagcgaatct | 360 |
| ggtcaatgca agctttaat attaatctct ttaaactgac ttagcttttc atctctatgt | 420 |
| tctcatgcag ttgcagacat cttgctgtgg agaaatgaga agaaaccctt cgtttctttt | 480 |
| cttgtcctaa acttgtttta ttactggttc ttcttttctg gaaacacatt tacttcatct | 540 |
| gcagcccaac ttctgtttat atttgctgtt gctctctatg gagtctcttt tgtgccgtca | 600 |
| aagatgtaag tattggttcc agaactttac cattatagaa ggcagtgaaa ataagttgtg | 660 |
| ataccaaaat tgtcctatca aaggatgatg cacccatgta tatatatttc acctttgaaa | 720 |
| tctatatgca actaagtgac agattgattt attttgacag tttcgggttt caagtcaaca | 780 |

-continued

```
aaatacccc  atggagattt  gagatctccg  aatccgctgt  gagagatctt  agtagtgata    840
tcgtagttgt  ctggaatcaa  ggagttcgca  gtttttaaatc cttaagcagt  ggaggagact    900
ggatcaagtt  cttcaaggta  caattctact  ctttatgctc  accaaacatg  aaaaatatct    960
cattgctctc  gtttcctaaa  acaaaacata  aaaacagatt  gcaggatcac  tgtatctcct   1020
caaactgatt  gtatcccgtt  cattggcagc  atttcttttc  acaggtactc  gaacaaagct   1080
tttgttttca  cacttcataa  acatgattaa  caacttcata  aacatgatta  acaacttctt   1140
tatccataac  attttctcta  cgctttgctt  ggacagttat  gtcgttctca  ttcaccggtt   1200
tcttcatcta  cgagcaatac  gagcttgagc  tctaccacct  agcccggata  ttcgtcgaat   1260
gcttaacatt  tattaaaagg  atggtgatac  ctgtttctga  tgcttcatct  aaaccaatgt   1320
tcatgtgaag  cttccaaagt  cctccactaa  acgaacacca  acaatcccag  agactaattg   1380
cagttattag  atgtcttatg  tacaaacatt  atgctatcag  gatgtaatct  tcactgagag   1440
gggatggata  tatgattatt  tacgaatttg  ccataactac  tatcaaaatg  caccgttttg   1500
atccggtttc  caaaaaaaaa  agaaaaaaaa  ggaaagtatc  cttatatatc  ctttaaaagc   1560
cgccgcttcg  atattccctg  gcctctcttt  ctctcacaat  ctaatcttct  tcgtcttcaa   1620
actcaatcta  gggttctctt  ctcctctctg  taggtaggat  tttgaacacc  caaatctctc   1680
atcgaatttt  tcttgctcaa  cgtatcatcg  cacaattcgt  ctctcgtttt  ccgtcacgtg   1740
gataatcgaa  atctcataat  cccaaaggta  aacaatcaa  ttctgggatt  ggaattttgg   1800
atccatagga  tcgtcaattg  aaacaatccc  gatggcgtta  tctatgaagc  cattcagagc   1860
cgatgattcc  ggtttccagt  caaacaatct  ttgggtcggt  agcctaacgc  cggagacgac   1920
agagtcagat  ctgaccgagt  tgtttggaag  atacggcgat  attgatagaa  tcacggtgta   1980
ttcttcacga  ggctttgcgt  ttatatacta  cagacatgtg  gaggaagcag  tcgcagccaa   2040
agaggctctt  caaggagcaa  atttgaatgg  aagtcaaatt  aagatcgaat  acgcacgacc   2100
ggtttgttct  tatctatatc  ttcgtttgtt  ctctaacttt  gattgtcttt  tgtcaacgat   2160
tatactcttt  ttgcgaattc  atagtccagg  ttcacaaaac  tttgatgatg  cttgtttagt   2220
ccaaaaattt  cttgttgaat  ctgttttttt  tttcctcatc  gtacaaatca  aagtcgaaac   2280
ctagtttttt  tctattatac  gtcgttagct  taaggcgaaa  cctgatccga  tcgaaacgtc   2340 tttttctcaaa ttactttggt  tatatcgaac  tcgcgcaaag  ccaaaccaca  gagaagctct   2400 gcaaatttg  atgttaaagc  atatataact  cttagcgaat  gagctctgca  aaagaataca   2460
tcaaacacat  gtttactctc  gtttatgcga  agaaggttta  atccgattgt  cgtttatctg   2520
caaacttgta  tccgcgttta  gcagtctgat  ttcaggttcg  cttcagatgt  taaatctcac   2580
aagcttgagt  atgaatgtat  tgcgtactcc  actcgaaatt  cgcaatggtg  aaaatttgga   2640
agcgagcaaa  ctctatcatc  ggccaaacag  ataagaaatt  ttggagttta  aaagttcagt   2700
ttcctgcaaa  aatcaaaccg  cgtggagaaa  tttgtctatg  gcggtacgta  gatatcaata   2760
actgcatctg  cgaaacagaa  aattctggca  accgtatcgt  cctaactcct  agtatcgctg   2820
gcacatatcc  atatcagtgt  gagggagttt  tgggcttgtt  ttggctcgat  gcttcaggaa   2880
gacaaattac  gtggttgtta  aggcggctaa  ctctaccaat  cagaaacgct  ttattcgaag   2940
aaccatgttt  gttcctcaat  tcccatccct  acgtacaatc  tgggctttcc  cattgtagtt   3000
ccttaggaag  ttgacttctt  cacaaccatt  ctgggattgg  tacagttgca  gtggacaaga   3060
caaatattca  tttgcaggca  gactcaaatt  tcaatgtctt  gccggctttg  agtacttaaa   3120
```

```
tggagtgttc agggattggt ttatttggga ctcaggcaat ggataaagac aggaatgttt    3180
tgcagaaagt attaatgtct ttccggcttt ggggactaca tacttctcct acagacaaaa    3240
tctgatgttt aggcaagaga aactattaac actgatttaa tagagaaaga ggagatggtt    3300
tctccttgcg gcaattttat ttgtttagga aagcaattga tatgaattgg tgtcgtagtg    3360
tagttgaaat tactagttag tttgtgtgtt tagtttcctt gatgtttgat gctttattct    3420
tggcaaccta tctgggtagt atcgccttct tatcgacctt ttcttgttgc aggcaaaacc    3480
ttgtaagagt ctatgggtgg gtggaatcgg ccctaatgtc tccaaggatg acctggagga    3540
agagttcagc aagtttggga aaatcgagga ttttaggttt ctcagagaac gcaagacagc    3600
tttcattgat tattatgaga tggatgatgc tttacaggct aagagcatga atggaaagcc    3660
tatgggtggt agcttttttgc gtgttgattt tctccggtca caagcgccaa aaaaa        3715
```